United States Patent [19]

Baker

[11] Patent Number: 5,326,914
[45] Date of Patent: Jul. 5, 1994

[54] HOMOGENEOUS CATALYTIC HYDRODECHLORINATION OF CHLOROCARBONS

[75] Inventor: Ralph T. Baker, Wilmington, Del.

[73] Assignee: E. I. Du Pont de Nemours and Company, Wilmington, Del.

[21] Appl. No.: 68,444

[22] Filed: May 27, 1993

[51] Int. Cl.$^5$ ............................................. C07C 17/10
[52] U.S. Cl. .................................................... 570/176
[58] Field of Search ......................................... 570/178

[56] References Cited

U.S. PATENT DOCUMENTS 3,857,900 12/1974 Wilkinson .
5,136,113 8/1992 Rao .

FOREIGN PATENT DOCUMENTS 1578933 11/1980 United Kingdom .

OTHER PUBLICATIONS

Lokteva et al., Izv. Akad. Nauk, SSSR, Ser. Khim, 3:539–542 (1989).
Ferrughelli and Horvath, J. Chem. Soc., Chem. Commun., pp. 806–807 (1992).

Primary Examiner—Alan Siegel
Attorney, Agent, or Firm—Susan B. Evans

[57] ABSTRACT

This invention relates to a liquid phase process for the preparation of $R_f$CHXY by the homogeneous catalytic hydrodechlorination of $R_f$CClXY wherein X and Y are independently H, F, Cl or $R_f'$ provided X and Y are not both Cl, $R_f$ and $R_f'$ are independently F, $CF_3$, $(CF_2)_n$Cl or $(CF_2)_n CF_3$, and n is 1–4, by reacting the $R_f$CClXY with hydrogen while in solution with a Periodic Table Group 6–10 metal complex catalyst which contains tertiary Periodic Table Group 15 ligands without added base.

8 Claims, No Drawings

HOMOGENEOUS CATALYTIC HYDRODECHLORINATION OF CHLOROCARBONS

BACKGROUND OF THE INVENTION

This invention relates to a liquid phase process for the homogeneous catalytic hydrodechlorination of $R_fCClXY$ wherein X and Y are independently H, F, Cl or $R_f'$ provided X and Y are not both Cl, $R_f$ and $R_f'$ are independently F, $CF_3$, $(CF_2)_nCl$ or $(CF_2)_nCF_3$, and n is 1-4, by reacting the $R_fCClXY$ with hydrogen while in solution with a Periodic Table Group 6-10 metal complex catalyst which contains tertiary Periodic Table Group 15 ligands without added base to form $R_fCHXY$.

By Periodic Table Group, Applicant includes those elements organized in Groups described as the "new notation" in the Periodic Table appearing in the CRC Handbook of Chemistry and Physics, 67th Edition, CRC Press (1986-1987).

Chlorofluorocarbons are considered to be detrimental toward the Earth's ozone layer. There is a worldwide effort to develop processes that will replace one or more of the chlorine atom(s) in certain chlorofluorocarbons. For example, 1,1,1,2-tetrafluoroethane (HFC-134a), a hydrofhorocarbon is being considered as a replacement for dichlorodifluoromethane (CFC-12) in refrigeration systems because of its refrigerant properties and zero ozone depletion potential.

There is thus a need for manufacturing processes that provide fluorocarbons that contain less or ideally no chlorine.

One method of reducing the chlorine content of halogen-substituted hydrocarbons containing chlorine as well as fluorine is reacting such organic starting materials with hydrogen in the presence of a hydrogenation catalyst (e.g., supported Periodic Table Group 7-10 metal catalysts). British Patent Specification 1,578,933 discloses, for example, that HFC-134a can be prepared by the hydrogenolysis of 2,2-dichloro-1,1,1,2-tetrafluoroethane (CFC-114a) or 1,1,1,2-tetrafluorochloroethane (HCFC-124) over palladium on carbon or palladium on alumina hydrogenation catalysts. These processes are typically run in the gas or liquid phase with a solid heretogeneous catalyst.

The prior art (Lokteva et al., Izv. Akad. Nauk. SSSR, Set. Khim., 1989, (3), 539-42; Ferrughelli and Horvath, J. C. S., Chem. Commun., 1992, 806) teaches hydrodechlorination using soluble homogeneous catalysts which require an excess of added base (NaOH, $NEt_3$) for removal of the HCl product. The present invention requires no added base.

SUMMARY OF THE INVENTION

A process is provided in accordance with this invention for a liquid phase, homogeneous catalytic hydrodechlorination of a compound having the formula $R_fCClXY$ wherein X and Y are independently H, F, Cl or $R_f'$, provided X and Y are not both Cl; $R_f$ and $R_f'$ are independently F, $CF_3$, $(CF_2)_nCl$ or $(CF_2)_nCF_3$, and n is 1-4, which comprises reacting the compound with hydrogen while in a solution with a Periodic Table Group 6-10 metal complex hydrodechlorination catalyst containing tertiary Periodic Table Group 15 ligands, preferably phosphines, without added base, to form $R_fCHXY$.

DETAILS OF THE INVENTION

The CFC compounds used in the hydrodechlorination reaction of this invention are preferably those wherein $R_f$ is $CF_3$ and X is F and Y is H or Cl.

In accordance with this invention the CFC compounds to be hydrodechlorinated are reacted with hydrogen at an elevated temperature of from about 80° C. to about 200° C., preferably from about 100° C. to about 150° C., most preferably about 120° C.

The hydrodechlorination of CFCs is performed in liquid phase using well-known chemical engineering practice, which includes continuous, semi-continuous or batch operations. The hydrodechlorination process is typically achieved at atmospheric or superatmospheric pressures.

A conventional amount of $H_2$ is used. Generally, in order to provide substantial hydrodechlorination product yields, the amount of hydrogen used is at least stoichiometric.

The reaction takes place at a $H_2$ pressure of from about 100 to about 1000 psi ($10^6$ to $10^7$ Pa), preferably about 500 to about 1000 psi, more preferably about 500 psi.

In accordance with this invention the reaction between the CFC component, $H_2$ and catalyst takes place in solution. Solvents may include aromatics such as benzene or toluene and ethers such as THF or DME, preferably benzene or toluene. More preferably neat, i.e., no solvent is used, in which case the CFC reactants serve as the solvent.

In accordance with this invention, metal complex catalysts suitable for hydrodechlorination are provided which contain at least one metal preferably selected from the group consisting of molybdenum, tungsten, rhenium, iron, ruthenium, osmium, cobalt, rhodium, iridium, nickel, palladium and platinum. These metal complexes contain tertiary Group 15 ligands, selected from phosphines, arsines, stibines and bismuthines. Catalysts are more preferably Ru, Os, Rh, Ir, Pd, or Pt with a phosphine ligand, most preferably a Pd or Rh phosphine complex. The ligand may be of the formula (i) $ER_3$ wherein E is P, As, Sb, or Bi, and R is hydrocarbyl; or (ii) $1,2\text{-}(ER_2')_2C_6H_4$ or $1,n\text{-}(ER_2')_2(CH_2)_n$, where n is 1-6, preferably 3, and R' is hydrocarbyl, preferably aliphatic.

Hydrocarbyl is a straight chain, branched or cyclic arrangement of carbon atoms connected by single, double or triple bonds, substituted accordingly with hydrogen atoms. As used herein, hydrocarbyl groups may be aliphatic and/or aromatic.

Base is a non-metal containing compound which forms a salt with the HCl co-product of the hydrodechlorination.

In the specification and Examples the following abbreviations are used:
CFC—chlorofluorocarbon
THF—tetrahydrofuran
HDC—hydrodechlorination
NMR—nuclear magnetic resonance
GC/MS—gas chromotography/mass spectroscopy
DME—1,2-bis(dimethoxy)ethane
114a—$CFCl_2CF_3$
123—$CHCl_2CF_3$
124—$CHFClCF_3$
133a—$CH_2ClCF_3$
134a—$CH_2FCF_3$ 143a—$CH_3CF_3$
Ph—$C_6H_5$
$Pr^i$—isopropyl, i.e., $CH(CH_3)_2$
Hx—n-hexyl, i.e., $(CH_2)_5CH_3$
Cy—cyclohexyl
Me—methyl
Et—ethyl
psi—pounds per square inch (1 psi = $6.9 \times 10^3$ Pa)

EXAMPLES

The hydrodechlorination reactions described below were performed in 10 mL stainless steel shaker tubes which were loaded with catalyst, and if applicable solvent in a nitrogen-purged dry box. The gaseous reactants, e.g., $H_2$ and 114a, were then charged sequentially and the reaction heated. Upon termination of the reaction, a gas sample was obtained for product analysis by GC/MS. The tube was opened in the glove box and its contents were dissolved in cold toluene-$d_8$ and transferred to an NMR tube for analysis of products by $^{19}F$ and $^1H$ NMR.

Example 1

Example Showing Selectivity to 134a

A mixture of 45 mg (0.05 mmol) {(RhCl[1,2-$(Pr^i_2P)_2C_6H_4]\}_2$ and 0.8 g (4.7 mmol) $CFCl_2CF_3$(114a) in 5 mL of benzene was treated with $H_2$ at an initial pressure of 100 psi then heated at 150° C. for 20 hr to give 124, 134a, and 143a in a 1:13:5 ratio at 4% conversion (2 turnovers).

Example 2

Selectivity Decreases with Added Phosphine Ligand

A mixture of 45 mg (0.05 mmol) {RhCl[1,2-$(Pr^i_2P)_2C_6H_4]\}_2$, 31 mg (0.1 mmol) 1,2-$(Pr^i_2P)_2C_6H_4$ and 0.8 g (4.7 mmol) 114a in 5 mL of benzene was treated with $H_2$ (100 psi) at 150° C. for 20 hr to give 124, 134a, and 143a in a 9:13:3 ratio at 3% conversion (1.5 turnovers). Solvent addition products $PhCHFCF_3$ and $PhCClFCF_3$ were also formed.

Example 3

Productivity Improves with 3-Carbon Backbone Phosphine Ligand

A mixture of 83 mg (0.1 mmol) {RhCl[$Pr^i_2P(CH_2)_3PPr^i_2$]}$_2$ and 1.35 g (7.9 mmol) $CFCl_2CF_3$ (114a) in 50 mL of benzene was treated with $H_2$ (100 psi) at 150° C. for 16 hr to give $CHFClCF_3$ (124), $CH_2FCF_3$ (134a) and $CH_3CF_3$ (143a) in a 1:8:1 ratio at 10% conversion (4 turnovers). The catalyst residue consisted primarily of $RhHCl_2[Pr^i_2P(CH_2)_3PPr^i_2]$.

Example 4

HDC of 124 Using Ni

A mixture of 54 mg (0.1 mmol) Ni($\eta^4$-1,5-cyclooctadiene)[$(Cy_2PCH_2)_2$] and 0.8 g (5.9 mmol) 124 in 5 mL of benzene was treated with $H_2$ (1000 psi) at 120° C. for 20 hr to give $CH_2FCF_3$ (134a) and solvent addition product $PhCHFCF_3$ in a 3:5 ratio at 16% conversion (9.5 turnovers). Traces of unsaturates $CH_2=CF_2$ (1132a) and $CHF=CF_2$ (1123) were also formed.

Example 5

High Pressure $H_2$ Increases HDC Productivity

Identical to Example 4 but with only 100 psi $H_2$ conversion was only 2.5% (1.5 turnovers) and the ratio of 134a to $PhCHFCF_3$ was 1:3.

Example 6

Also Works for Pd

A mixture of 50 mg (0.07 mmol) Pd[1,2-$(Pr^i_2P)_2C_6H_4]_2$ and 3.4 g (2.5 mmol) 124 was treated with $H_2$ (1000 psi) at 200° C. for 20 hr to give 134a and traces of unsaturates at 6.5% conversion (23 turnovers).

Example 7

HDC Productivity Insensitive to T>150° C.

Identical to Example 6 but with 3.1 g (22.7 mmol) 124 and at 150° C. conversion to 134a and traces of unsaturates was 6% (19.5 turnovers).

Example 8

High Selectivity Using Rh with No Solvent

A mixture of 40 mg (0.05 mmol) {RhCl[$(Pr^i_2PCH_2)_2$]}$_2$ and 3 g (22 mmol) 124 was treated with $H_2$ (1000 psi) at 150° C. for 20 hr to give >98% 134a at 6% conversion (13 turnovers).

Example 9

Higher Pressure $H_2$ Increases HDC Productivity at Expense of 134a Selectivity

A mixture of 40 mg (0.05 mmol) {RhCl[$(Pr^i_2PCH_2)_2$]}$_2$ and 3.7 g (21.8 mmol) 114a was treated with $H_2$ (1000 psi) at 150° C. for 20 hr to give 124, 134a, and 143a in a 2:1:2.5 ratio at 7.5% conversion (20 turnovers). Trace amounts of methane, ethane and 133a were also observed.

Example 10

Lower Selectivity to 134a with Added Phosphine Ligand

A mixture of 40 mg (0.05 mmol) {RhCl[$(Pr^i_2PCH_2)_2$]}$_2$, 26 mg (0.1 mmol) $(Pr^i_2PCH_2)_2$ and 3.5 g (20.6 mmol) 114a was treated with $H_2$ (1000 psi) at 150° C. for 20 hr to give 124, $CH_2ClCF_3$ (133a), $CHCl_2CF_3$ (123) and 134a in a 17:4:1 ratio at 10.5% conversion (26 turnovers).

Example 11

Higher Selectivity to 134a Using 3-Carbon Backbone Phosphine Ligand

A mixture of 41 mg (0.05 mmol) {RhCl[$(Pr^i_2P(CH_2)_3PPr^i_2)$]}$_2$ and 3.5 g (20.6 mmol) $CFCl_2CF_3$ (114a) was treated with $H_2$ (1000 psi) at 150° C. for 20 hr to give 124, 134a and 143a in a 1:3.5:3.5 ratio at 9.5% conversion (24 turnovers). Also observed minor amount (ca. 4% of total products) of $CH_2ClCF_3$ (133a).

Example 12

Preferred Rh Catalyst at 120° C., 500 psi $H_2$

Identical to Example 11, except pressure of $H_2$ is 500 psi and temperature is 120° C. The reaction gave 134a:143a:124:133a in a ratio of 30:19:3.5:1 at 3% conversion (6 turnovers).

Example 13

Also Works for Pd

A mixture of 33 mg (0.05 mmol) Pd[Pr$^i_2$P(CH$_2$)$_3$P-Pr$^i_2$]$_2$ and 3.5 g (20.6 mmol) 114a was treated with H$_2$ (1000 psi) at 150° C. for 20 hr to give 124, 133a, 123 and 134a in a 12:1.5:1:1 ratio at 5.5% conversion (14 turnovers).

Example 14

Also Works with Arylphosphine Ligands

A mixture of 26 mg (0.05 mmol) Pd{[Ph$_2$P(CH$_2$)$_2$]$_2$}$_2$ and 3.5 g (20.6 mmol) 114a was treated with H$_2$ (1000 psi) at 150° C. for 20 hr to give 124, 134a, 143a, 123, and 133a in a 8:3:1.5:1.2:1 ratio at 6% conversion (14 turnovers). A trace of CH$_2$=CF$_2$ (1132a) was also observed.

Example 15

HDC Activity Decreases with Certain Phosphine Ligands

A mixture of 24 mg (0.05 mmol) Pd[(Pr$^i_2$PCH$_2$)$_2$]$_2$ and 3.5 g (20.6 mmol) 114a was treated with H$_2$ (1000 psi) at 150° C. for 20 hr to give 124 and 123 in a 20:1 ratio at 1.5% conversion (6 turnovers).

Example 16

Also Works with Ir

A mixture of 58 mg (0.05 mmol) IrCl(PPh$_2$Hx)$_3$ and 3.5 g (20.6 mmol) 114a was treated with H$_2$ (1000 psi) at 150° C. for 20 hr to give 124, 133a, 123 and 134a in a 30:1.2:1:1.2 ratio at 16% conversion (40 turnovers). Some ethene and propene was also observed.

Example 17

Also Works with Ru

A mixture of 29 mg (0.05 mmol) RuCl$_2$[(Et$_2$PCH$_2$)$_2$]$_2$ and 3.5 g (20.6 mmol) 114a was treated with H$_2$ (1000 psi) at 150° C. for 20 hr to give 124, 123, 133a, and 134a in a 83:3:3:1 ratio at 11% conversion (45 turnovers). Some unsaturates were also observed.

Example 18

Also Works with Ru and ER$_3$-Type Phosphines

A mixture of 24 mg (0.05 mmol) RuCl$_2$(PMe$_3$)$_4$ and 3.5 g (20.6 mmol) 114a was treated with H$_2$ (1000 psi) at 150° C. for 20 hr to give 124, 133a, 123, 134a, and 143a in a 36:3:2.5:2:1 ratio at 5.5% conversion (22.5 turnovers). Some unsaturates were also observed.

Example 19

Also Works with Os

A mixture of 28 mg (0.05 mmol) OsCl$_2$(PMe$_3$)$_4$ and 3.5 g (20.6 mmol) 114a was treated with H$_2$ (1000 psi) at 150° C. for 20 hr to give 124, 134a, 123 and 133a in a 54:3:3:2 ratio at 10% conversion (41 turnovers). Some unsaturates were also observed.

Example 20

Also Works with Pt

A mixture of 43 mg (0.05 mmol) Pt(PEt$_2$Ph)$_4$ and 3.5 g (20.6 mmol) 114a was treated with H$_2$ (1000 psi) at 150° C. for 20 hr to give 124, 133a, 134a, and 123 in a 52:3:2.5:2 ratio at 2.5% conversion (10.5 turnovers). Some unsaturates were also observed.

Example 21

Also Works for Mo

A mixture of 22 mg (0.05 mmol) ($\eta$-C$_5$Me$_5$)MoCl(N$_2$)(PMe$_3$)$_2$ and 3.5 g 114a was treated with H$_2$ (1000 psi) at 150° C. for 20 hr to give 124, 134a, 123 and 133a in a ratio of 14.5:3:2.5:2 at 2% conversion (8 turnovers).

What is claimed is:

1. A liquid phase process for the homogeneous catalytic hydrodechlorination of a compound having the formula R$_f$CClXY wherein X and Y are independently H, F, Cl or R$_f'$ provided X and Y are not both Cl; R$_f$ and R$_f'$ are independently F, CF$_3$, (CF$_2$)$_n$Cl or (CF$_2$)$_n$CF$_3$, and n is 1–4, which comprises reacting the compound with hydrogen while in solution with a Periodic Table Group 6–10 metal complex hydrodechlorination catalyst containing tertiary Periodic Table Group 15 ligands, without added base, to form R$_f$CHXY, wherein the Periodic Table Group 6–10 metal is selected from Re, Mo, W, Fe, Ru, Os, Co, Rh, Ir, Ni, Pd, and Pt, with the tertiary Periodic Table Group 15 ligand selected from phosphine, arsine, stibine, and bismuthine.

2. A process according to claim 2 wherein the temperature is from about 80° to about 200° C. and the pressure is from about 100 to about 1000 psi.

3. A process according to claim 2 wherein the temperature is from about 100° to about 150° C. and the pressure is about 500 psi.

4. A process according to claim 3 wherein R$_f$ is CF$_3$, X is F and Y is H or Cl.

5. A process according to claim 4 wherein the Periodic Table Group 6–10 metal is Ru, Os, Rh, Ir, Pd, or Pt with phosphine ligands.

6. A process according to claim 5 wherein the catalyst is a Pd or Rh phosphine complex.

7. A liquid phase process for the homogeneous catalytic hydrodechlorination of CFCl$_2$CF$_3$ which comprises reacting CFCl$_2$CF$_3$ with H$_2$ in a benzene solution with a {RhCl[1,2-(Pr$^i_2$P)$_2$C$_6$H$_4$]} catalyst at an initial pressure of 100 psi and a temperature of 150° C. to form CH$_2$FCH$_3$.

8. A liquid phase process for the catalytic hydrodechlorination of CFCl$_2$CF$_3$ which comprises reacting neat CFCl$_2$CF$_3$ with H$_2$ with {RhCl[Pr$^i_2$P(CH$_2$)$_3$P-Pr$^i_2$]}$_2$ at an initial pressure of 500 psi at a temperature of 120° C. to form CH$_2$FCF$_3$.

* * * * *